US009242049B2

(12) United States Patent
Engle

(10) Patent No.: US 9,242,049 B2

(45) Date of Patent: Jan. 26, 2016

(54) ULTRASONIC SUSPENSION DELIVERY SYSTEM

(75) Inventor: Robb W. Engle, Kingston, NY (US)

(73) Assignee: Sono-Tek Corporation, Milton, NY (US)

( * ) Notice: Subject to any disclaimer, the term of this patent is extended or adjusted under 35 U.S.C. 154(b) by 737 days.

(21) Appl. No.: 13/495,886

(22) Filed: Jun. 13, 2012

(65) Prior Publication Data

US 2012/0241478 A1 Sep. 27, 2012

Related U.S. Application Data

(63) Continuation-in-part of application No. 12/098,679, filed on Apr. 7, 2008, now Pat. No. 8,226,599.

(60) Provisional application No. 61/041,853, filed on Apr. 2, 2008.

(51) Int. Cl.
*A61M 5/315* (2006.01)

(52) U.S. Cl.
CPC ................................ *A61M 5/31596* (2013.01)

(58) Field of Classification Search
CPC ................ A61M 37/0092; A61M 2205/3693; A61M 11/005; A61M 2205/058; A61M 35/00; A61M 5/31596
USPC ..................................................... 604/22, 82
See application file for complete search history.

(56) References Cited

U.S. PATENT DOCUMENTS

| | | | | |
|---|---|---|---|---|
| 5,516,043 | A * | 5/1996 | Manna et al. | 239/102.2 |
| 2006/0025716 | A1* | 2/2006 | Babaev | 604/22 |
| 2009/0254020 | A1* | 10/2009 | Engle | 604/22 |

* cited by examiner

*Primary Examiner* — Kami A Bosworth
*Assistant Examiner* — Brandy S Lee
(74) *Attorney, Agent, or Firm* — Miles & Stockbridge PC

(57) ABSTRACT

An ultrasonic suspension delivery system is provided. The system includes an ultrasonic energy source and an ultrasonic resonating syringe electrically coupled thereto. The ultrasonic resonating syringe includes a barrel with a nozzle, and an ultrasonic resonating plunger slidingly displaceable within the barrel. The ultrasonic resonating syringe includes front and rear bodies, front and rear transducers, and front and rear horns. A support member or a transition member may also be included.

16 Claims, 5 Drawing Sheets

ULTRASONIC SUSPENSION DELIVERY SYSTEM

CROSS-REFERENCE TO RELATED APPLICATIONS

This application is a Continuation-in-Part (CIP) of U.S. patent application Ser. No. 12/098,679, filed on Apr. 7, 2008, which claims priority to U.S. Provisional Patent Application No. 61/041,853, filed on Apr. 2, 2008, the disclosures of which are incorporated herein by reference in their entirety.

FIELD OF THE INVENTION

The present invention relates to suspension delivery systems, and, more particularly, to ultrasonic suspension delivery systems.

BACKGROUND OF THE INVENTION

Scientists, technicians and others often have problems delivering precise proportions of solid particles dispersed in a fluid to a surface. Inconsistent mixture ratios bring about waste when solid particles settle out of the fluid, such as, for example, suspensions delivered by a syringe. Solid particles that settle out of the fluid may remain in the syringe as waste material, which may be hazardous, time consuming and costly to dispose of properly.

Known suspension delivery systems may suffer from uneven distribution of solid particles in the fluid. For example, a 10 cc suspension may have a higher concentration of solid particles in the lower portions of the device, and a lower concentration of solid particles in the upper portions of the device. Accordingly, the concentration or ratio of solid particles to fluid varies as the suspension is delivered to the surface. Additionally, suspended particles may begin to settle well before the suspension is delivered, for example, when the suspension begins flowing from a mixing chamber.

Accordingly, there is a need to keep the solid particles suspended in the fluid at all times during delivery.

SUMMARY OF THE INVENTION

Embodiments of the present invention advantageously provide an ultrasonic suspension delivery system that includes an ultrasonic energy source and an ultrasonic resonating syringe electrically coupled thereto. The ultrasonic resonating syringe includes a barrel with a nozzle, and an ultrasonic resonating plunger slidingly displaceable within the barrel. The ultrasonic resonating plunger includes front and rear bodies, front and rear transducers, and front and rear horns. A support member or a transition member may also be included.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

Figure 1:
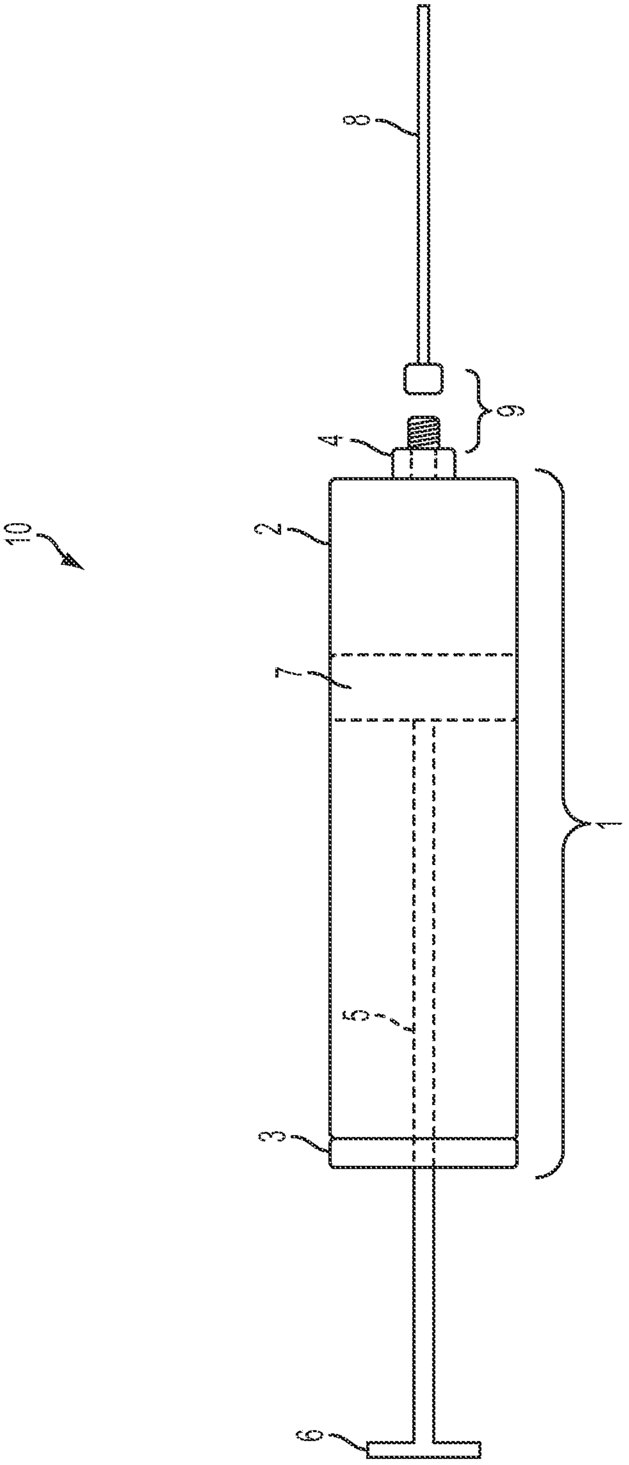
FIG. 1 depicts a schematic illustration of a known fluid delivery device.

The invention will now be described with reference to the drawing figures, in which like reference numerals refer to like parts throughout.

A known fluid delivery device or syringe 10 is schematically illustrated in FIG. 1.

Barrel 1 includes a cylindrical tube 2 with a removable end cap 3 at one end (i.e., the proximal end), and a nozzle 4 at the other end (i.e., the distal end) with a bore through which liquid flows. Plunger 5 is slidingly disposed within barrel 2, and includes a central shaft with a handle 6 mounted on one end (i.e., the proximal end), and a piston 7 mounted on the other end (i.e., the distal end). The central shaft passes through a bore in removable end cap 3. Piston 7 fits tightly against the inner surface of barrel 2 to create a seal that prevents air from flowing around piston 7 towards nozzle 4, and fluid from flowing around piston 7 and towards end cap 3. A needle or cannula 8 may be connected to nozzle 4 using cooperating threaded or locking connectors 9; other components may also be connected to nozzle 4, such as, for example an intravenous (IV) tube, a spraying device, an atomizer, etc.

To deliver fluid through syringe 10, a volume of fluid is first drawn into barrel 2 through nozzle 4 by moving plunger 5 from the distal end of barrel 2 towards the proximal end of barrel 2. Plunger 5 can be moved by hand, or plunger 5 can be connected to a syringe pump (not shown). A volume of fluid is delivered through the bore in nozzle 4 by moving plunger 5 back towards the distal end of barrel 5. With respect to delivering suspensions, syringe 10 suffers from many of the aforementioned problems.

Embodiments of the present invention provide an ultrasonic suspension delivery system that includes an ultrasonic energy source and an ultrasonic resonating syringe electrically coupled thereto. The ultrasonic resonating syringe includes a barrel with a nozzle, and an ultrasonic resonating plunger slidingly displaceable within the barrel. The ultrasonic resonating plunger agitates the suspension using ultrasonic energy, which quickly and uniformly disperses agglomerated particles and advantageously holds these particles evenly suspended for long periods of time. In preferred embodiments, the ultrasonic resonating syringe nozzle is fluidically coupled to an ultrasonic atomizer, and the ultrasonic resonating syringe plunger is mechanically coupled to, and articulated by, a syringe pump.

Figure 2:
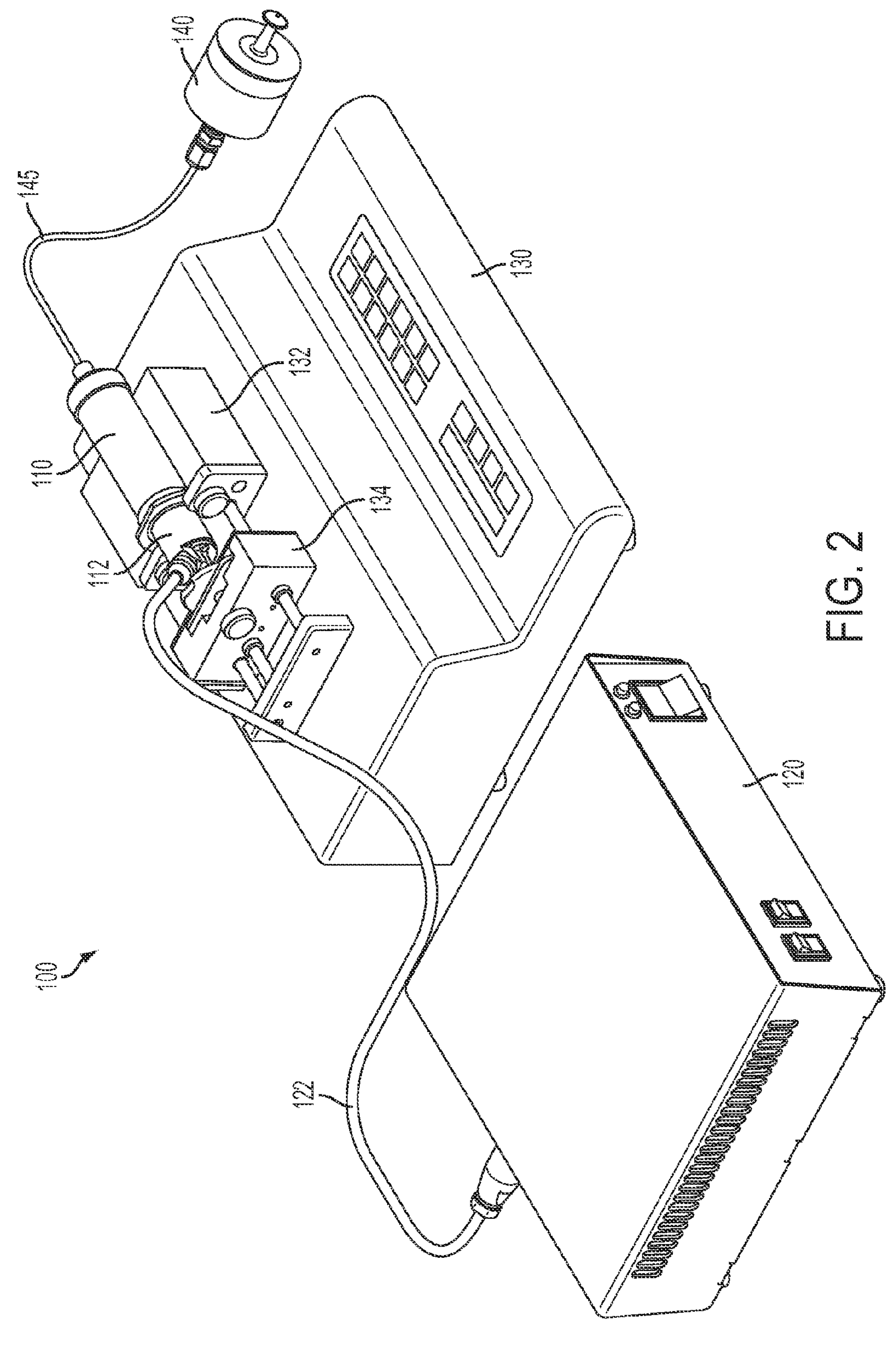
FIG. 2 presents a perspective view of an ultrasonic suspension delivery system according to an embodiment of the present invention.

FIG. 2 presents a perspective view of an ultrasonic suspension delivery system 100 according to an embodiment of the present invention.

Ultrasonic resonating syringe 110 is electrically coupled to ultrasonic energy source 120 using an electrical cable 122, such as, e.g., a shielded or unshielded twisted pair cable, a coaxial cable, etc. Ultrasonic resonating syringe 110 is mechanically coupled to syringe pump 130 using, e.g., a support cradle 132 and pusher block 134, etc., and fluidically coupled to ultrasonic atomizer 140 using, e.g., tubing 145, etc. The syringe pump 130 articulates the ultrasonic resonating plunger 112 of ultrasonic resonating syringe 110, while ultrasonic atomizer 140 applies the suspension. Ultrasonic resonating syringe 110 must be periodically refilled, of course, and the syringe pump 130 may include valves and tubes coupled to a suspension source to facilitate this process.

In one embodiment, the electrical cable includes a threaded, Euro-style M12 connector at the ultrasonic energy source 120, and a soldered connection at the ultrasonic resonating syringe 110. In another embodiment, the electrical cable includes a SubMiniature version A (SMA) or BNC connector at the ultrasonic resonating syringe 110 and/or the ultrasonic energy source 120. Other cables and connectors are also contemplated by the present invention. In many embodiments, the ultrasonic energy source 120 operates in the frequency range of 20,000 to 120,000 Hz.

Figure 3:
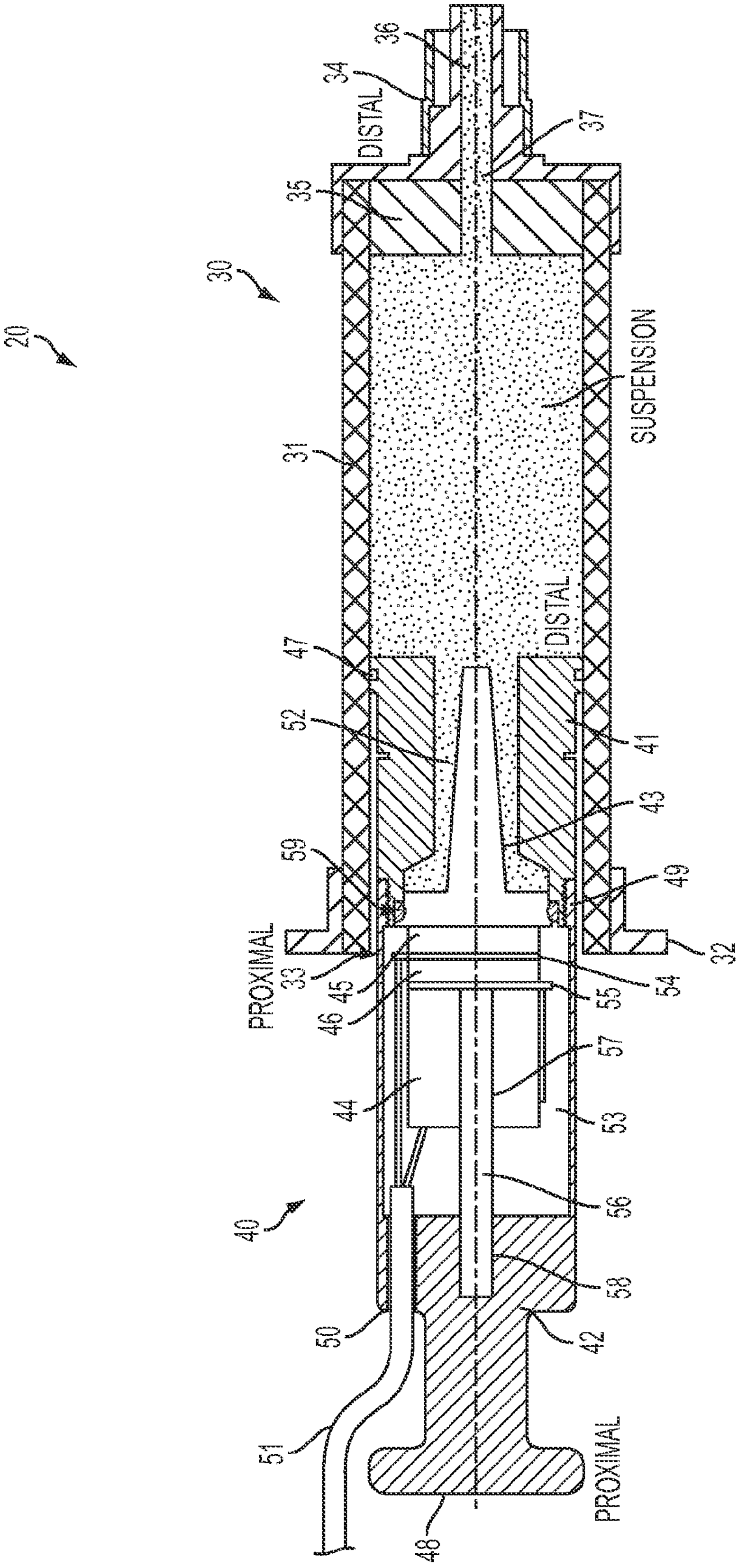
FIG. 3 presents a right side sectional view of an ultrasonic resonating syringe according to an embodiment of the present invention.
Figure 4:
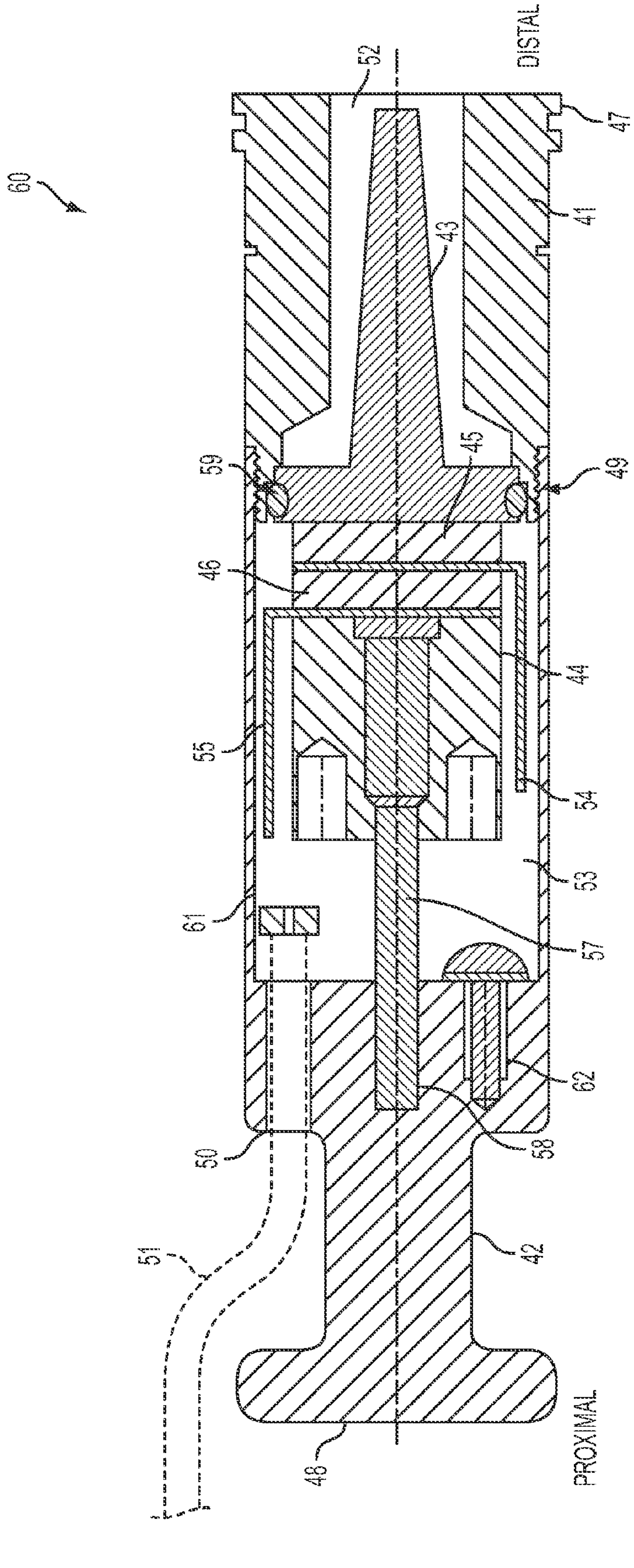
FIG. 4 presents a right side sectional view of an ultrasonic resonating plunger according to an embodiment of the present invention.

FIG. 3 presents a right side sectional view of an ultrasonic resonating syringe 20, including barrel 30 and ultrasonic resonating plunger 40, according to an embodiment of the present invention. FIG. 4 presents a right side sectional view of an ultrasonic resonating plunger 60, according to another embodiment of the present invention.

Barrel 30 includes a cylindrical tube 31 with inner and outer surfaces, a proximal end with a flange 32 and an opening 33, and a distal end with a nozzle 34 having a bore 36 therethrough. Cylindrical tube 31 is preferably transparent, semi-transparent or translucent, and may be formed from glass, plastic, etc. Alternatively, cylinder tube 31 may be opaque and formed from titanium, aluminum, stainless steel, etc. Plunger stop 35 may be provided within cylindrical tube 31, and abuts the proximal end of nozzle 34. A bore 37 is provided through plunger stop 35 to fluidically couple the interior of cylindrical tube 31 and the bore of the nozzle 34. Alternatively, the proximal end of nozzle 34 functions as a plunger stop.

Ultrasonic resonating plunger 40 is slidingly displaceable within barrel 30 for pushing the fluid, suspension, etc. toward the distal opening thereof, e.g., bores 36, 37. Ultrasonic resonating plunger 40 includes a front body 41, a rear body 42, a front horn 43, a rear horn 44, a front ultrasonic transducer 45, a rear ultrasonic transducer 46.

Front body 41 has a central bore 52 extending therethrough, and may be formed from Teflon, for example. The distal end of front body 41 includes a seal 47 that engages the inner surface of the cylindrical tube 31 to prevent air from flowing around front body 41 towards nozzle 34, and to prevent suspension from flowing around front body 41 and towards opening 33. Rear body 42 includes a central bore 53 extending partially therethrough, a proximal end having a handle 48, and a distal end attached to the proximal end of front body 41 using, for example, threaded connection 49. Rear body 42 may be formed from aluminum, stainless steel, titanium, etc., nylon, Teflon, etc. Rear body 42 also includes a bore 50 through which an electrical cable 51 passes.

Front horn 43 is disposed within the central bore 52 of front body 41, while rear horn 44 is disposed within the central bore 53 of the rear body 42. Front horn 43 and rear horn 44 may be formed from titanium, for example, which has a high tensile strength to density ratio, high corrosion resistance, and an ability to withstand moderately high temperatures without creeping. Materials with the similar characteristics are also contemplated. Front ultrasonic transducer 45 abuts the proximal end of front horn 43, while rear ultrasonic transducer 46 abuts the distal end of rear horn 44. Positive electrode 54 is disposed between front ultrasonic transducer 45 and rear ultrasonic transducer 46, while negative electrode 55 is disposed on the rear ultrasonic transducer 46. Electrical cable 51 is connected to positive electrode 54 and negative electrode 55.

Support member 56 passes through a central bore 57 in rear horn 44, and includes a proximal end seated within cavity 58 disposed in the proximal end of central bore 53 of rear body 42, and a distal end that abuts rear ultrasonic transducer 46. Support member 56 aligns and supports the resonating horn/transducer subassembly, and O-ring 59 resiliently couples front horn 43 to the proximal end of front body 41.

Ultrasonic resonating syringe 20 employs ultrasonic sound waves at frequencies beyond the range of human hearing, i.e., above about 20,000 Hz. Front and rear ultrasonic transducers 45, 46 convert electrical energy, received from ultrasonic energy source 120, into mechanical energy, which is transmitted to front and rear horns 43, 44. A longitudinal standing wave is created, and the length of the resonating horn/transducer subassembly, consisting of front horn 41, front and rear transducers 45, 46, positive and negative electrodes 54, 55, and rear horn 44, determines the resonant frequency in accordance with several mathematical relationships, including:

$f:c/\lambda$ frequency f is proportional to the speed of sound c through a material divided by the wavelength $\lambda$;

$\lambda:L$ wavelength $\lambda$ is proportional to length L; and $c:\sqrt{(B/\rho)}$ speed of sound c through a material is proportional to the square root of the bulk modulus B divided by the density of the material $\rho$.

In operation, a low power alternating current (AC) is provided to ultrasonic resonating plunger 40 at a resonant frequency of the resonating horn/transducer subassembly, which creates a nodal plane at positive electrode 54 and an anti-nodal plane at each end of the resonating horn/transducer subassembly. The shape of front horn 43 amplifies the motion at the front anti-nodal plane, which agitates the suspension within barrel 31.

With respect to ultrasonic resonating plunger 60 depicted in FIG. 4, electrical cable 51 may include a SubMiniature version A (SMA) 61 connector; other connectors are also contemplated. Ground screw 62 may also be provided.

Figure 5A:
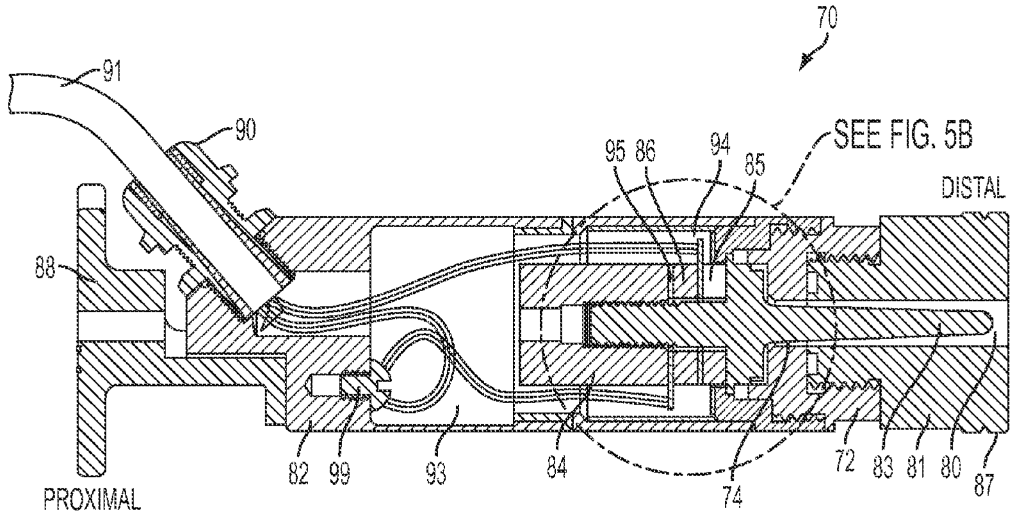
FIG. 5A presents a right side sectional view of an ultrasonic resonating plunger.
Figure 5B:
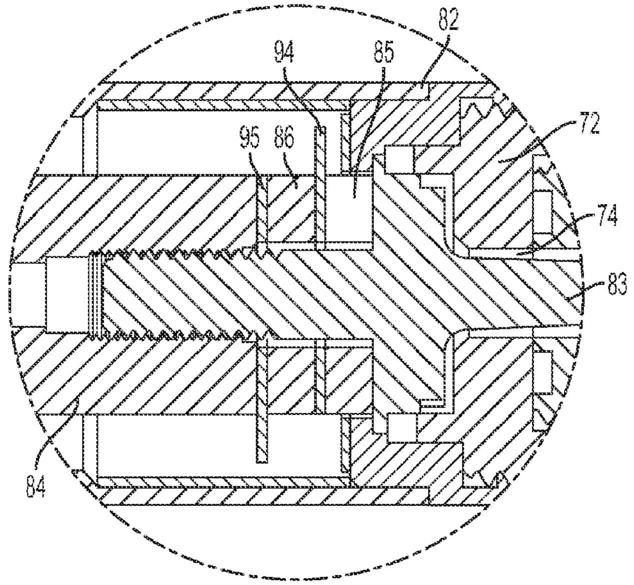
FIG. 5B presents a close up view of a central section thereof, according to another embodiment of the present invention.

FIG. 5A presents a right side sectional view of an ultrasonic resonating plunger 70, including a close up view of a central portion thereof (FIG. 5B), according to another embodiment of the present invention.

Ultrasonic resonating plunger 70 includes a front body 81, a rear body 82, a front horn 83, a rear horn 84, a front ultrasonic transducer 85, a rear ultrasonic transducer 86 and a transition member 72.

Front body 81 has a central bore 80 extending completely therethrough, and may be formed from Teflon, for example. The distal end of front body 81 includes a seal 87 that engages the inner surface of the cylindrical tube to prevent air from flowing around front body 81 towards nozzle, and suspension from flowing around front body 81 and towards the opening in the barrel. Rear body 82 includes a central bore 93 extending partially therethrough, a proximal end having a handle 88, and a distal end. Rear body 82 may be formed from aluminum, stainless steel, titanium, etc., nylon, Teflon, etc. Rear body 82 also includes a connector 90 through which an electrical cable 91 passes.

Front horn 83 is disposed within the central bore 92 of front body 81, while rear horn 84 is disposed within the central bore 93 of the rear body 82. Front horn 83 and rear horn 84 may be formed from titanium, for example, which has a high tensile strength to density ratio, high corrosion resistance, and an ability to withstand moderately high temperatures without creeping. Materials with the similar characteristics are also contemplated. Front ultrasonic transducer 85 abuts the proximal end of front horn 83, while the rear ultrasonic transducer 86 abuts the distal end of rear horn 84. Positive electrode 94 is disposed between front ultrasonic transducer 85 and rear ultrasonic transducer 86, while negative electrode 95 is disposed on the rear ultrasonic transducer 86. Electrical cable 91 is connected to positive electrode 94 and negative electrode 95.

Rather than support member 56, ultrasonic resonating plunger 70 includes a transition member 72 to align and support the resonating horn/transducer subassembly within front and rear bodies 81, 82. Transition member 72 is threadedly coupled to the proximal end of front body 81 as well as to the distal end of rear body 82; other mechanical couplings are also contemplated. Transition member 72 may be formed from stainless steel, titanium, aluminum, etc., and includes a central bore 74 extending therethrough.

Front and rear ultrasonic transducers 85, 86 include central bores extending respectively therethrough, while rear horn 84 includes a threaded, central bore extending partially therethrough. The proximal end of front horn 83 extends through the central bores of front and rear ultrasonic transducers 85, 86, and is threadedly coupled to the central bore of rear horn 84.

Advantageously, transition member 72 allows the resonating horn/transducer subassembly to float freely in the central bore 93 of rear body 82, and the nodal plane passes through the threaded couplings of transition member 77, resulting in very little movement. This configuration provides improved performance over ultrasonic resonating plunger 60.

The many features and advantages of the invention are apparent from the detailed specification, and, thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and, accordingly, all suitable modifications and equivalents may be resorted to that fall within the scope of the invention.

What is claimed is:

1. An ultrasonic suspension delivery system, comprising:
- an ultrasonic energy source;
- an ultrasonic resonating syringe, electrically coupled to the ultrasonic energy source, including:
  - a barrel including a cylindrical tube with an inner surface, a proximal end with an opening, and a distal end with a nozzle, and
  - an ultrasonic resonating plunger, slidingly displaceable within the barrel, including:
    - a front body including a central bore extending therethrough, a proximal end, and a distal end with a seal to engage the inner surface of the barrel,
    - a rear body including a central bore extending partially therethrough, a proximal end with a handle, and a distal end removably coupled to the proximal end of the front body,
    - a front horn, disposed within the central bore of the front body, resiliently coupled to the proximal end of the front body,
    - a front ultrasonic transducer, disposed within the central bore of the rear body, abutting the proximal end of the front horn,
    - a rear ultrasonic transducer, disposed within the central bore of the rear body, abutting the front ultrasonic transducer, and
    - a rear horn, disposed within the central bore of the rear body, abutting the rear ultrasonic transducer; and
- a syringe pump, connected to the handle of the ultrasonic resonating plunger, including:
  - a cradle to support the barrel, and
  - a pusher block, connected to the handle, to slidingly displace the ultrasonic resonating plunger within the barrel.

2. The ultrasonic suspension delivery system according to claim 1, wherein distal end of the rear body is removably coupled to the proximal end of the front body by a threaded connection.

3. The ultrasonic suspension delivery system according to claim 2, wherein the front horn is resiliently coupled to the proximal end of the front body by an O-ring.

4. The ultrasonic suspension delivery system according to claim 3, further comprising a support member, passing through a central bore in the rear horn, having a proximal end seated within a cavity disposed in the proximal end of the central bore of the rear body, and a distal end abutting the rear ultrasonic transducer.

5. The ultrasonic suspension delivery system according to claim 4, further comprising:
- a positive electrode disposed between the front and rear ultrasonic transducers; and
- a negative electrode disposed on the proximal end of the rear ultrasonic transducer, wherein, in operation, the front and rear ultrasonic transducers generate a standing wave that has a nodal plane proximate to the positive electrode.

6. The ultrasonic suspension delivery system according to claim 5, wherein, in operation, the front and rear ultrasonic transducers generate a standing wave that has an anti-nodal plane proximate to the distal end of the front horn.

7. The ultrasonic suspension delivery system according to claim 1, wherein the ultrasonic energy source operates in the frequency range of 20,000 to 120,000 Hz.

8. The ultrasonic suspension delivery system according to claim 1, further comprising an ultrasonic atomizer fluidically coupled to the barrel nozzle.

9. An ultrasonic suspension delivery system, comprising:
- an ultrasonic energy source; and
- an ultrasonic resonating syringe, electrically coupled to the ultrasonic energy source, including:
  - a barrel including a cylindrical tube with an inner surface, a proximal end with an opening, and a distal end with a nozzle, and
  - an ultrasonic resonating plunger, slidingly displaceable within the barrel, including:

a front body including a central bore extending therethrough, a proximal end, and a distal end with a seal to engage the inner surface of the barrel, a rear body including a central bore extending partially therethrough, a proximal end with a handle, and a distal end, a transition member, including a central bore extending therethrough, coupled to the proximal end of the front body and the distal end of the rear body by a threaded connection, a front horn including a distal portion disposed within the central bores of the front body and the transition member, and a proximal portion disposed within the central bore of the rear body, a front ultrasonic transducer, including a central bore extending therethrough, abutting the proximal portion of the front horn, a rear ultrasonic transducer, including a central bore extending therethrough, abutting the front ultrasonic transducer, a rear horn abutting the rear ultrasonic transducer and coupled to the proximal portion of the front horn by a threaded connection.

10. The ultrasonic suspension delivery system according to claim 9, further comprising:

a positive electrode, including a central bore extending therethrough, disposed between the front and rear ultrasonic transducers; and a negative electrode, including a central bore extending therethrough, disposed on the proximal end of the rear ultrasonic transducer, wherein, in operation, the front and rear ultrasonic transducers generate a standing wave that has a nodal plane proximate to the transition member.

11. The ultrasonic suspension delivery system according to claim 10, wherein, in operation, the front and rear ultrasonic transducers generate a standing wave that has an anti-nodal plane proximate to the distal end of the front horn.

12. The ultrasonic suspension delivery system according to claim 9, wherein the ultrasonic energy source operates in the frequency range of 20,000 to 120,000 Hz.

13. The ultrasonic suspension delivery system according to claim 9, further comprising an ultrasonic atomizer fluidically coupled to the barrel nozzle.

14. The ultrasonic suspension delivery system according to claim 9, further comprising:

a syringe pump, connected to the handle of the ultrasonic resonating plunger, including:

a cradle to support the barrel, and a pusher block, connected to the handle, to slidingly displace the ultrasonic resonating plunger within the barrel.

15. The ultrasonic suspension delivery system according to claim 14, wherein the syringe pump periodically refills the ultrasonic resonating syringe barrel.

16. An ultrasonic resonating plunger, comprising:

a front body including a central bore extending therethrough, a proximal end, and a distal end with a seal to engage the inner surface of a syringe barrel;

a rear body including a central bore extending partially therethrough, a proximal end with a handle, and a distal end;

a transition member, including a central bore extending therethrough, coupled to the proximal end of the front body and the distal end of the rear body by a threaded connection;

a front horn including a distal portion disposed within the central bores of the front body and the transition member, and a proximal portion disposed within the central bore of the rear body;

a front ultrasonic transducer, including a central bore extending therethrough, abutting the proximal portion of the front horn;

a rear ultrasonic transducer, including a central bore extending therethrough, abutting the front ultrasonic transducer; a positive electrode, including a central bore extending therethrough, disposed between the front and rear ultrasonic transducers;

a negative electrode, including a central bore extending therethrough, disposed on the proximal end of the rear ultrasonic transducer; and a rear horn abutting the negative electrode and coupled to the proximal portion of the front horn by a threaded connection, wherein, in operation, the front and rear ultrasonic transducers generate a standing wave that has a nodal plane proximate to the transition member and an anti-nodal plane proximate to the distal end of the front horn.

* * * * *